United States Patent [19]

Willis et al.

[11] 4,424,146
[45] Jan. 3, 1984

[54] ACETALDEHYDE ETHYL 6-DIHYDROLINALYL ACETAL PERFUME COMPOSITIONS

[75] Inventors: Brian J. Willis, Ramsey; Michael R. Britten-Kelley, Metuchen, both of N.J.; Odd Hansen, Jackson Heights, N.Y.

[73] Assignee: Fritzsche Dodge & Olcott Inc., New York, N.Y.

[21] Appl. No.: 309,388

[22] Filed: Oct. 7, 1981

[51] Int. Cl.³ .......................... A61K 7/46; C11B 9/00; C07C 43/00; C07C 79/34
[52] U.S. Cl. ................................. 252/522 R; 568/590
[58] Field of Search ..................... 568/590; 252/522 R

[56] References Cited

U.S. PATENT DOCUMENTS

| | | | |
|---|---|---|---|
| 3,745,189 | 7/1973 | Hoffmann et al. | 252/522 R X |
| 3,869,517 | 3/1975 | Gradeff et al. | 252/522 R X |
| 3,948,814 | 4/1976 | Rijke | 252/522 R |
| 4,173,543 | 11/1979 | Mussinan et al. | 252/522 R X |

FOREIGN PATENT DOCUMENTS 7111071  2/1973  Netherlands .................... 252/522 R Primary Examiner—Helen M. S. Sneed
Attorney, Agent, or Firm—Cooper, Dunham, Clark, Griffin & Moran

[57] ABSTRACT

The present invention relates to the novel compound acetaldehyde ethyl 6-dihydrolinalyl acetal, useful as a fragrance material. The invention also provides a method of preparing this compound from 6-dihydrolinalool, and fragrance compositions which include the compound.

2 Claims, No Drawings

ACETALDEHYDE ETHYL 6-DIHYDROLINALYL ACETAL PERFUME COMPOSITIONS

BACKGROUND OF THE INVENTION

Acetaldehyde ethyl linalyl acetal (I):

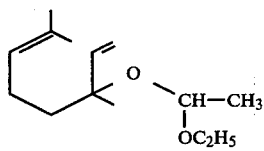

exhibits useful olfactory and perfumery properties (D. de Rijke, U.S. Pat. No. 3,948,814). It is reported to have "an exalting flower odor, related to the odor of hydroxycitronellal", and it is claimed to give a "flower-like undertone" to perfume compositions.

THE INVENTION

The subject of the present invention is the novel compound acetaldehyde ethyl 6-dihydrolinalyl acetal (II):

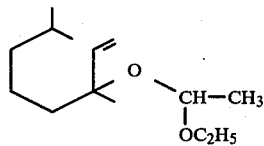

which has not been described previously in the literature. Acetaldehyde ethyl 6-dihydrolinalyl acetal is believed to be an intermediate in the synthesis of 5,9-dimethyl-4-decenal although it has not been referred to specifically, and has not been isolated and characterized (R. Marbet and G. Saucy, Helv. Chim. Acta, 50, 2095 (1967); German Auslegeschrift 1,193,490). Suprisingly, acetaldehyde ethyl 6-dihydrolinalyl acetal (II), although similar in structure to (I), is very different in odor character, possessing tart, green, fresh, sweet, coriander, herbaceous, laurine, lilial, lyral, fruity, jammy, flower shop and calamus notes. By comparison, acetaldehyde ethyl linalyl acetal (I) has a fatty, earthy, linalool note. We also note that whereas the acetal (I) resembles linalool in odor properties, the acetal (II) is entirely different from 6-dihydrolinalool. The addition of the same amount of one or the other of these acetals to a neroli composition (Example II below) has a completely different effect on the composition.

The acetaldehyde ethyl tetrahydrolinalyl acetal (III) and acetaldehyde ethyl dehydrolinalyl acetal (IV) have been prepared in order to compare their organoleptic properties

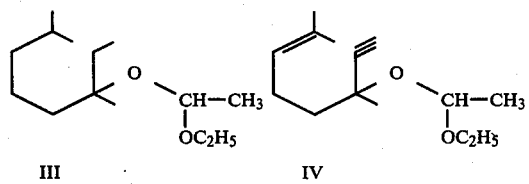

with those of the compound of the present invention, acetaldehyde ethyl 6-dihydrolinalyl acetal (II). The compound of structure (III) has an odor very similar to that of tetrahydrolinalool, and is not sufficiently different to be of interest in its own right. The compound of structure (IV) has a woody, floral, slightly green character with poor tenacity, and is likewise of little interest. These results show that the compound claimed is not one of a series of analogous compounds with similar odor properties; in fact, the compound claimed differs from the analogous compounds in both odor quality and strength. Addition of (II) to various perfume compositions (see Examples) imparts a greener, more lemony and floral character to the original product, showing that (II) is clearly valuable for use in fragrance compositions where such notes are required.

The preparation of acetaldehyde ethy 6-dihydrolinalyl acetal may be accomplished by addition of a catalytic amount of concentrated hydrochloric acid to a mixture of 6-dihydrolinalool and ethyl vinyl ether, as described in the following Example.

EXAMPLE I

A 2 L reaction flask equipped with mechanical stirrer, thermometer, and reflux condenser, is charged with 6-dihydrolinalool (156 g) and ethyl vinyl ether (360 g). A portion of concentrated hydrochloric acid (1 ml) is added to the stirred mixture, followed by a second portion (1 ml) after 1 h. After standing at room temperature for 16 h, the reaction mixture is washed with 5% sodium bicarbonate (300 ml) and water (300 ml). The organic layer is separated and excess ethyl vinyl ether removed by distillation at atmospheric pressure through a 30 cm column packed with 0.75 cm Raschig rings. The residue is then distilled at reduced pressure through the same apparatus to give acetaldehyde ethyl 6-dihydrolinalyl acetal (190.8 g, 84%) b.p. 104°–106°/50 mm, $n_D^{20}$ 14320–14322, GLC purity 99%.

The following Example illustrates the contrasting effects of the compound of Example I and acetaldehyde ethyl linalyl acetal (I) on a neroli perfume composition.

EXAMPLE II

| Perfume composition "neroli" | |
|---|---|
| Indole | 3 parts by weight |
| Nerolidol | 25 |
| cis-Jasmone | 1 |
| Geraniol (pure) | 50 |
| Geranyl acetate | 25 |
| Hydroxy citronellal | 10 |
| Linalool (synthetic) | 500 |
| Linalyl acetate | 300 |
| Phenyl ethyl alcohol | 20 |
| Terpineol | 30 |
| Methyl anthranilate | 5 |
| d-Limonene | 31 |
| | 1000 parts by weight |

Addition of 100 parts by weight of the compound of Example I imparts a limey, cardamon topnote and a smooth creamy effect to the above composition. In contrast, addition of 100 parts by weight of (II) imparts an earthy character and does not improve the overall effect.

The following Examples further illustrate the utility of acetaldehyde ethyl 6-dihydrolinalool acetal of Example I in different fragrances.

EXAMPLE III

| Perfume composition "jasmin (absolute)" | |
| --- | --- |
| Indole | 15 parts by weight |
| Methyl anthranilate | 5 |
| para-Cresol | 5 |
| cis-3-Hexenol | 2 |
| cis-Jasmone | 40 |
| Eugenol | 15 |
| cis-3-Hexenyl benzoate | 20 |
| Nerolidol | 30 |
| Benzyl alcohol | 30 |
| Benzyl acetate | 250 |
| Benzyl benzoate | 488 |
| Linalool (synthetic) | 100 |
| | 1000 parts by weight |

Addition of 100 parts by weight of the compound of Example I to the above composition enhances the lemony, floral character and makes the odor richer and creamier.

EXAMPLE IV

| Perfume composition "muguet" | |
| --- | --- |
| Indole | 5 parts by weight |
| Benzyl alcohol | 200 |
| Geranyl acetate | 10 |
| Citronellyl propionate | 30 |
| Phenyl ethyl alcohol | 90 |
| Citronellyl formate | 10 |
| Terpineol | 60 |
| Linalool synthetic | 50 |
| Jasmin absolute (synthetic) | 30 |
| Citral | 4 |

Addition of 100 parts by weight of the compound of Example I to the above composition enhances the lemony floral richness.

What is claimed is:

1. The compound acetaldehyde ethyl 6-dihydrolinalyl acetal, having the formula:

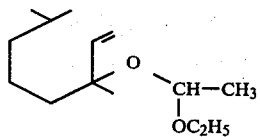

2. A fragrance composition which comprises an amount of the compound of claim 1 effective to impart fragrance thereto.

* * * * *